(12) United States Patent
Niu

(10) Patent No.: US 6,198,025 B1
(45) Date of Patent: Mar. 6, 2001

(54) METHODS FOR EFFECTUATING MRNA TRANSFER OF GENETIC INFORMATION BETWEEN SPECIES AND PRODUCT OF THE SAME

(76) Inventor: Man C. Niu, 7950 Montgomery Ave., Elkins Park, PA (US) 19027

( * ) Notice: Subject to any disclaimer, the term of this patent is extended or adjusted under 35 U.S.C. 154(b) by 0 days.

(21) Appl. No.: 08/796,641

(22) Filed: Feb. 7, 1997

Related U.S. Application Data

(60) Provisional application No. 60/012,122, filed on Feb. 9, 1996.

(51) Int. Cl.[7] .............................. A01H 5/00; A01H 9/00; A01H 11/00
(52) U.S. Cl. ................... 800/300.1; 800/298; 800/295; 800/320.1
(58) Field of Search .................................. 435/69.1, 419; 800/205, DIG. 56, 278, 284, 290, 295, 320.1, 300.1, 298

(56) References Cited

PUBLICATIONS

Potrykus. Ann. Review of Plant Physiol. 1991. vol. 42: 205–225.*
Napoli et al. The Plant Cell. 1989. vol. 2: 278–289.*
Carvalaho et al. The EMBO Journal. 1992. vol. 11: 5995–5602.*
Plant Cell Tissue Organ Culture. 1995. vol. 40: 1–15.*
Topfer et al. Plant Cell. 1989. Jan. issue. vol. 1: 133–139.*
Gallie et al. Plant Cell Reports. 1993. vol. 13: 119–122.*
Kagawa and Hirano. 1989. Nucleic Acid Research. 1989. vol. 17: 886.*
Feldmann and Marks. Molecular and General Genetics. 1987. vol. 208: 1–9.*
Ausubel et al.Short Protocols in Molecular Biology. 1989.*

* cited by examiner

*Primary Examiner*—Paula Hutzell
*Assistant Examiner*—Ousama Zaghmout
(74) *Attorney, Agent, or Firm*—Charles N. Quinn

(57) ABSTRACT

The present invention provides methods for the beneficial genetic transformation of plants based on transfer of genetic information mediated by mRNA rather than DNA. mRNA was extracted from the cotyledon and sprout of soybean and both mRNAs were separately used to treat corn kernels which were then planted. The results of protein extraction and analysis revealed that these corn kernels contained soy globulin. Furthermore, Southern and Western blotting techniques confirmed that this soy mRNA-induced soy globulin protein was encoded by soy DNA which was incorporated into the corn genome and transmitted to subsequent generations of corn.

2 Claims, 6 Drawing Sheets

METHODS FOR EFFECTUATING MRNA TRANSFER OF GENETIC INFORMATION BETWEEN SPECIES AND PRODUCT OF THE SAME

CROSS-REFERENCED TO RELATED PATENT APPLICATION

This patent application is based on and entitled to the benefit of the filing date of provisional U.S. patent application Ser. No. 60/012,122 filed Feb. 9, 1996 in the name of Man C. Niu.

FIELD OF THE INVENTION

This invention relates to the fields of molecular biology and genetic engineering. More specifically, the invention provides methods of introducing foreign genetic material (mRNA) into plants.

INCORPORATION BY REFERENCE

The following publications are referenced in this application by numerals in parenthesis:
1. Niu, M. C., L. C. Niu, C. Ma, Z. P. Lin and Y. L. Zhang (1980). Genetic manipulation in higher organisms. III. Detection of soy protein in seeds derived from soy mRNA-treated rice. *Scientia Sinica,* 23: 119–122.
2. Laemmli, U. K. (1970). Cleavage of structural proteins during the assembly of the head of bactiophage $T_4$. *Nature,* 227: 681–685.
3. Vaessen, R. T. M. J., J. Kreke and G. S. P. Groot (1981). Protein transfer to nitrocellulose filters. A simple method for quantitation of simple proteins in complex mixtures. FEBS letter 124: 193–196.
4. Mishra, N. C., M. C. Niu and E. L. Tatum (1975). Induction by RNA of inositol independence in *Neurospora crassa. Proc. Nat. Acad. Sci.,* 72: 642–645.
5. Szkukalek, A., And F. Solymosy (1994). Molecular characterization of two tomato U6RNA pseudogenes generated by RNA-mediated mechanisms. *Plant Science* 99:183–187.

Each of these publications is incorporated herein by reference; numbers in the text referring to these publications correspond to the numbers set forth above.

BACKGROUND OF THE INVENTION

Methods of improving various crops are known. Some of these methods involve introducing foreign, i.e. nonendogenous, DNA into plant cells or tissues and analyzing the resulting plants for presence of exogenous nucleic acid and expression of the foreign gene. Although successful in certain instances, these methods are laborious, time consuming and variable in their reproducibility. There exists a need for the further development of methods for the beneficial genetic transformation of agricultural crops to increase protein yields or otherwise improve crops for human and/or animal consumption.

SUMMARY OF THE INVENTION

In one of its aspects, this invention provides methods for producing transgenic plants by introduction therein of foreign mRNA, to impart to the resulting transgenic plants capability of synthesizing the foreign protein in subsequent generations. Based on the transfer of genetic information via mRNA molecules, as opposed to DNA molecules, in one of its aspects the invention provides a distinct improvement over methods presently employed in the art. Endogenous proteins of plants are beneficially augmented with valuable proteins from foreign sources utilizing the methods of this invention.

In another of its aspects, this invention embraces a transgenic plant expressing beneficial exogenous proteins produced by obtaining a sample of mRNA encoding the exogenous protein, incubating and inoculating seed of the plant with the mRNA under conditions whereby the mRNA enters the seed, germinating the seed and growing the transgenic plant from the seed. Desirably the sample of mRNA is obtained from soybeans, most desirably from soybean cotyledons or sprouts. Further desirably, the plant is corn and most desirably corn strain 27-1 or 85089.

In another of its aspects, this invention embraces a transgenic corn plant expressing soy globulin protein. Most desirably in this aspect of the invention the corn is strain 27-1; alternatively the corn may be strain 85089.

In a preferred practice of the invention, mRNA from soy cotyledon is isolated and purified and used for microinjection of corn seed from corn strain 27-1. The treated seeds are then germinated and resulting plants assayed for exogenous protein expression.

Following microinjection and transformation, protein presence and content in propagated transgenic corn plants is analyzed by Ouchterlony immunodiffusion assays sodium dodecyl sulfate polyacrylamide gel electrophoresis (SDS-PAGE) followed by Western blotting. The presence of soy DNA in the transformed corn is confirmed by Southern blotting using soy globulin specific radiolabeled DNA probes.

In alternative embodiments of the invention, mRNA may be isolated from soy sprouts. Additionally, other strains of corn may be utilized, including corn strain 85089. The mRNA may be microinjected into recipient seeds once or twice or even more times. The methods described result in successful production of transgenic corn plants expressing soy globulin protein, as set forth in Table 1, below.

Figure 1:
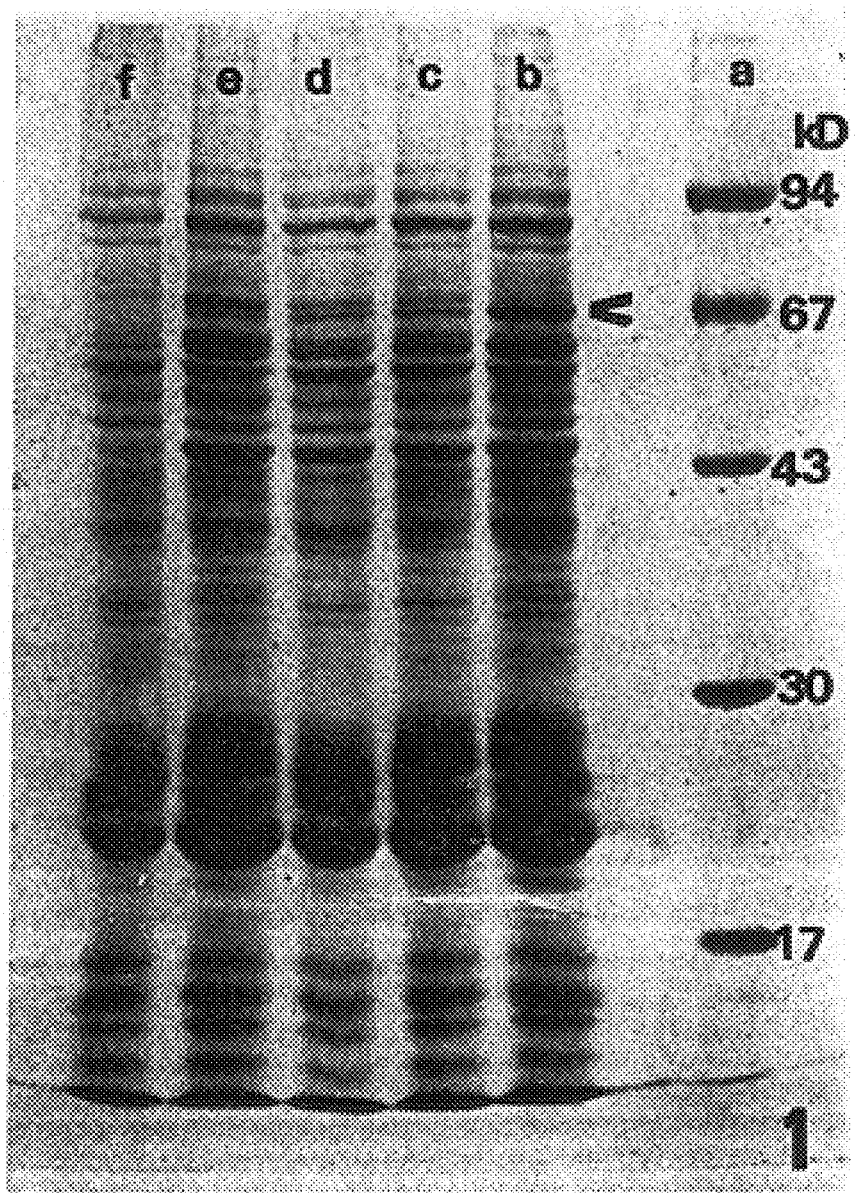
FIG. 1 depicts a representative SDS-PAGE gel of protein extracted from kernels of the soy cotyledon mRNA-treated corn. A control sample from untreated corn is shown in lane (f). The arrow points to the additional band in lanes b–e (at 67 KD); no band is observed in lane f; lane (a) is a M.W. marker.

DETAILED DESCRIPTION OF THE PREFERRED EMBODIMENTS AND BEST MODE KNOWN FOR PRACTICING THE INVENTION

Methods of the invention entail isolation and purification of mRNA from sprouts or cotyledons of the soybean. Following isolation, mRNA is microinjected separately into corn strains 85089 and 27-1. Following transformation, protein content in the resulting generations of corn was analyzed. The presence of soy globulin in the treated corn was demonstrated via immunological and biochemical methods.

Experimental data, which is set forth in detail hereinbelow, show that soy mRNA microinjection results in the generation of transgenic corn plants which synthesize soy globulin. It appears that the soy mRNA has been reverse transcribed and incorporated into the corn genome. Thus, soy mRNA-induced globulin was expressed in succeeding generations of corn. The presence of soy globulin nucleic acid sequences was demonstrated by Southern blotting of the transformed corn DNA with complementary $^{32}$P-labeled soy globulin probes.

The following definitions are provided to facilitate understanding of the invention:

mRNA: Messenger Ribonucleic Acid is a temporary complementary copy of the sense strand of protein coding DNA. In eukaryotes, this major intermediate of gene expression is transcribed from protein coding genes by RNA polymerase II. It is usually transcribed as a relatively long pre-mRNA which is then processed, still within the nucleus. Further post-transcriptional modifications are made to most eukaryotic mRNA's to add a 5' cap structure and a 3' poly A tail.

Transgenic Plants: Plants which have been engineered via recombinant nucleic acid techniques to express exogenous proteins encoded by other plants or animals.

Southern Hybridization Analysis: A technique developed by Edward Southern in 1975 in which denatured DNA is transferred from agarose gels in which fragments have been separated by electrophoresis to a nitrocellulose or a nylon membrane laid over the gel, before hybridization with a complementary nucleic acid probe. This step is required as hybridization to the gel itself is very inefficient. The technique is ubiquitous in molecular genetics and its numerous applications usually revolve around the identification of a particular DNA sequence within a mixture of restriction fragments, for example to determine the presence, position, and number of copies of a gene in the genome. It is also an integral technique used in DNA typing.

Western Blotting: A method for detecting one or more specific proteins in a complex protein mixture such as a cell extract, which is named by analogy with Southern hybridization to detect DNA sequences and Northern blotting to detect RNA's. The procedure involves fractionating the protein mixture by denaturing SDS-PAGE gel electrophoresis and transferring and immobilizing the mixture onto a solid membrane of either nitrocellulose or nylon by electroblotting. The loaded membrane is then incubated with an antibody raised against the protein of interest. The antibody-antigen complex so formed on the membrane can then be detected by a procedure which involves the application of a secondary antibody, raised against the first antibody, and to which an enzyme has been covalently linked. The insoluble reaction product generated by enzyme action can then be used to indicate the position of the target protein on the membrane.

Ouchterlony Double Agar Immunodiffusion Assay: An assay in which antigen and antibody are placed in wells cut in an agar gel which then diffuse towards one another and precipitate to form an opaque line in the region where they meet in optimal proportions. A preparation containing several antigens often gives rise to multiple lines. The immunological relationship between two antigens can then be assessed by setting up precipitation reactions in adjacent wells: The lines formed by each antigen may be completely confluent, indicating immunological identity. They may show a spur, as in the case of partially related antigens, or they may cross, indicative of unrelated antigens.

The means for practicing the methods of the invention are described in detail below:

Isolation of mRNA: The cotyledon and/or sprouts (shoot and root axis) of the germinating soybean were used for the extraction of mRNA according to published procedures (1). Eighty percent of the poly A mRNA in soy encodes soy globulin protein (11S and 7S).

Microinjection of Corn Seeds: Corn seeds from strains 27-1 and 85089 were treated separately and analyzed as follows: 200 corn seeds, i.e. kernels as a batch were washed twice using tap water. They were then soaked in double distilled water at 4° C. for 48 to 72 hours. During this time the water was changed 2 or 3 times. The imbibed seeds were then microinjected with soy mRNA, (isolated from either soy sprout or soy cotyledon) using a commercially available microinjector which is a graduated glass tube of 100 microliter capacity with a stainless steel needle attached. The needle was inserted into the seed as close to the central axis as possible. The amount injected was 1 microgram of soy mRNA in 1 microliter of double distilled water. Over 90% of the injected seeds germinated and grew into corn plants.

Protein Extraction from the Corn Kernels: Groups of six kernels were soaked overnight in double distilled water at 4° C. After removing the outer skin they were dehydrated by acetone soakings, then de-fatted by ether soakings and then ground into a fine powder. Protein was extracted with 3 ml of extraction fluid (10% glycerine, 5% 2-mercaptoethanol, 2.3% SDS, 8 M/L urea, 0.02% of bromophenol blue in 0.625 M/L Tris-HCl, pH 6.8). The sediment was removed by centrifugation (4000 rpm for 10 minutes.). The supernatant was boiled 3 mins. and centrifuged (5000 rpm for 5 minutes.). The supernatant was then stored at −20° C. for future analysis.

SDS-PAGE: Using the discontinuous SDS-PAGE procedure (2), the extracted protein was separated into a series of bands and stained with Coomassie brilliant blue R250.

Ouchterlony Double Agar Immunodiffusion Test: The plate used for the test was made of 1.2% agar. Rabbit anti-soy protein serum was used to detect the presence or absence of soy protein in the mRNA-treated kernels and untreated control samples.

Detection of Soy Protein by Western Blotting Technique: The additional band obtained from the sodium dodecyl sulfate polyacrylamide gel electrophoresis (SDS-PAGE) test was transferred to a nitrocellulose membrane (3). The membrane was washed with the following buffer: (0.02 M/L Tris buffered saline (TBS), pH 7.4, and 0.05% Tween 20 (TTBS)) and sealed in a dark chamber containing 4% Bovine serum albumin (BSA) in TTBS at 30° C. for two hours. After washing with TTBS fluid the soy protein was detected by the ProtoBlot Western Blot AP System according to Promega's technical manual.

Detection of Soy DNA by Molecular Southern Hybridization: DNA was extracted from the soy mRNA treated and control corn samples. The DNAs were electrophoresed on gels and transferred to a nitrocellulose membrane. Commercial reverse transcriptase was used to catalyze the transcription of soy mRNA into cDNA (5). This cDNA was nick translated into $^{32}$P-labelled cDNA. Southern blotting analysis was carried out on the treated and control corn DNAs with $^{32}$P-labeled cDNA probes complementary to soy mRNA; see FIG. 6. Appearance of hybridization bands demonstrates presence of the soy globulin DNA sequences in the treated corn. In control samples, the hybridization band is absent. Lane S, soy DNA control; Lane C, DNA isolated from uninjected, control corn samples; Lanes 1–5, DNA isolated from soy mRNA treated corn from different fields. The arrowhead indicates the hybridizing band.

The following example is provided to illustrate a preferred practice of the invention; it is not intended to limit the invention in any way:

EXAMPLE I

Genetic transformation of plants based on transfer of information encoded by mRNA, rather than DNA, has been demonstrated in corn. mRNA was extracted from the cotyledon and sprout of the soybean and both mRNA's were separately introduced into corn kernels which were then planted.

Protein extraction, followed by biochemical analyses revealed that these corn kernels express soy globulin. Additionally, the presence of soy mRNA-induced soy globulin protein was demonstrated in subsequent generations of corn by Western blotting.

DNA isolated from corn treated with soy globulin mRNA was subjected to Southern hybridization analysis with $^{32}$P-labeled cDNA probes specific for soy globulin RNA. This revealed presence of soy globulin nucleotide sequences in the treated corn.

These results demonstrate the feasibility of creating valuable transgenic plants via introduction of mRNA's encoding agronomically important proteins.

Genetic transformation of economically important plant species is highly desirable.

To date, strategy for gene transfer in plants often involves introduction of foreign DNA into protoplasts or callus to enable its introduction into the nuclear genome. However, regeneration of certain plant species from protoplasts so transformed has been difficult to achieve. This invention describes transforming capacity of soy globulin mRNA in corn. The results achieved indicate that delivery of genetic information by mRNA molecules is useful for the stable transformation of monocot species. The method of the invention using mRNA molecules represents a more reliable means of introducing new genes into plants than that provided by the transfer of genetic information using heterologous DNA. Furthermore, mRNA induced genetic changes are stable, whereas genetic changes induced by DNA are not (4).

Two strains of high yield corn, 85089 and 27-1, were utilized for transformation in these experiments: Total RNA was isolated from powdered soybeans, either cotyledon or sprouts, by the cold phenol extraction procedure and purified by oligo DT chromatography. The mRNA thus isolated was adjusted to 1 microgram per microliter; 1 microliter of the resulting solution was injected separately into kernels of imbibed corn. The injected seeds from the two different strains were sown in rows separated by a passageway, in a garden measuring 10×12 m$^2$. The planting of strain 85089 was done in late April and strain 27-1 in late May. The difference in planting dates was done to avoid cross-hybridization. Uninjected corn kernels (control) were sown in a field several miles away. Over 90% of the uninjected and soy mRNA-injected seeds germinated and grew into plants. All were harvested in October.

The methods of the present invention were performed using corn strains, 27-1 and 85089. mRNA used for microinjection was prepared from at least two sources in the soy plant, e.g. the cotyledons and the sprouts.

Microinjected corn seeds were planted and the corn kernels of the first generation were harvested. SDS-PAGE of isolated corn protein from the first generation revealed an additional band at approximately 67 KD. A representative gel is shown in FIG. 1. Ouchterlony double agar immunodiffusion assays using rabbit anti-soy protein serum demonstrated that the additional band was of soy origin and due to the presence of soy protein globulin. The kernels of the first generation were then planted in order to see if the soy protein globulin was transmitted to the next generation.

Extracts from the kernels of the first generation of corn were analyzed for detection of soy protein as follows: SDS-PAGE: The corn kernels of one ear of corn constituted one sample. A total of 134 samples were analyzed from the mRNA-treated group and 10 from the control. Of the 134 samples in the mRNA-treated group, 29 exhibited an additional band, and the balance did not. In FIG. 1, an additional band is observed at 67 KD in the treated corn extracts. No new band is observed in control extracts isolated from untreated corn (lane f).

The data obtained from SDS-PAGE analysis of 134 samples of mRNA treated corn are summarized in Table 1. When soy cotyledon mRNA is microinjected once into corn strains 85089 and 27-1, 18.75% of the 85089 corn plants demonstrate an additional band, whereas 23.68% of the 27-1 corn plants demonstrate an additional band . Hence, strain 27-1 is more efficiently transformed than strain 85089. This is further supported by data obtained when each strain, 27-1 and 85089, is microinjected twice with mRNA isolated from soy cotyledon. In these experiments, 26.47% of the 27-1 corn plants exhibited an additional band, as compared to 20% of the 85089 corn plants, as set forth in Table 1.

Soy sprout mRNA was microinjected once or twice into corn strain 85089. The data indicate that a second injection of soy sprout mRNA into corn strain 85089 did not result in an increase in the number of plants exhibiting an additional band, as set forth in Table 1, below.

Comparing results obtained following microinjection of corn strain 85089 with mRNA from the cotyledon or the sprout shows that mRNA isolated from soy cotyledon is more efficient in generating transgenic corn plants than mRNA isolated from the soy sprout, as set forth in Table 1, below:

TABLE 1

FREQUENCY OF FORMATION OF THE mRNA-INDUCED ADDITIONAL BAND IN THE CORN PROTEIN AS SHOWN BY SDS-PAGE

| EXPERIMENTS RESULTS | EXPERIMENTAL SERIES | | | | | | CONTROL SERIES | |
|---|---|---|---|---|---|---|---|---|
| SOURCE OF mRNA | SOY COTYLEDON | | | | SOY SPROUT | | NONE | |
| NUMBER OF mRNA TREATMENTS | ONCE | | TWICE | | ONCE | TWICE | NONE | |
| STRAIN OF CORN USED | 85089 | 27.1 | 85089 | 27.1 | 85089 | 85089 | 85089 | 27.1 |
| NUMBER OF SAMPLES TESTED | 16 | 38 | 15 | 34 | 18 | 13 | 5 | 5 |
| No. OF SAMPLES EXHIBITING ADDITIONAL BAND | 3 | 9 | 3 | 9 | 3 | 2 | 0 | 0 |
| PERCENT OF SAMPLES EXHIBITING AN ADDITIONAL BAND | 18.75% | 23.68% | 20.0% | 26.47% | 16.67% | 15.38% | 0% | 0% |

Figure 2:
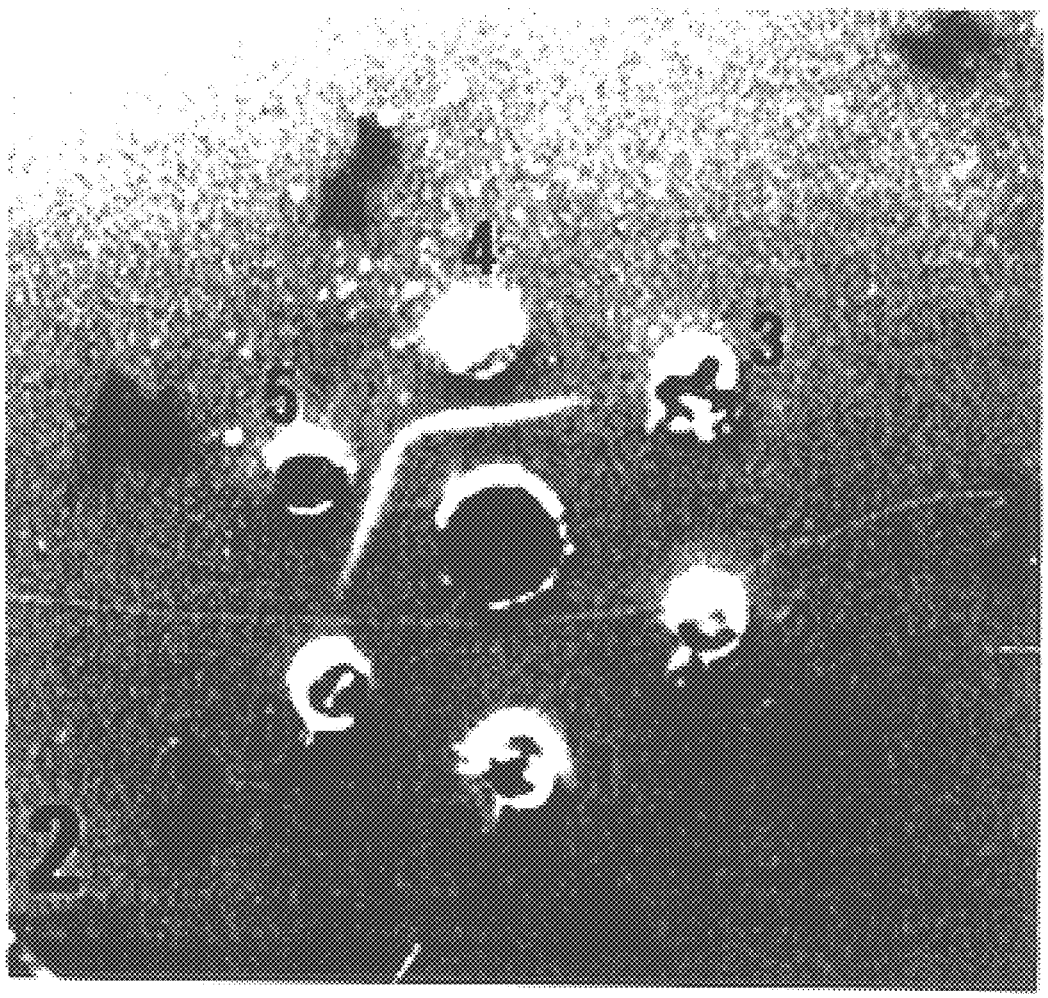
FIG. 2 shows the results of a double agar Ouchterlony immunodiffusion assay used to detect the presence of soy protein in kernels isolated from corn strain 85089. The central well contains the antibody and peripheral wells 1–3 contain proteins from the mRNA-treated corn kernels which do not demonstrate an additional band; wells 4 and 5 contain proteins from the soy globulin mRNA-treated kernels exhibiting an additional band. The presence of the additional band results in the formation of a precipitation line; well 6 is a negative control.
Figure 3:
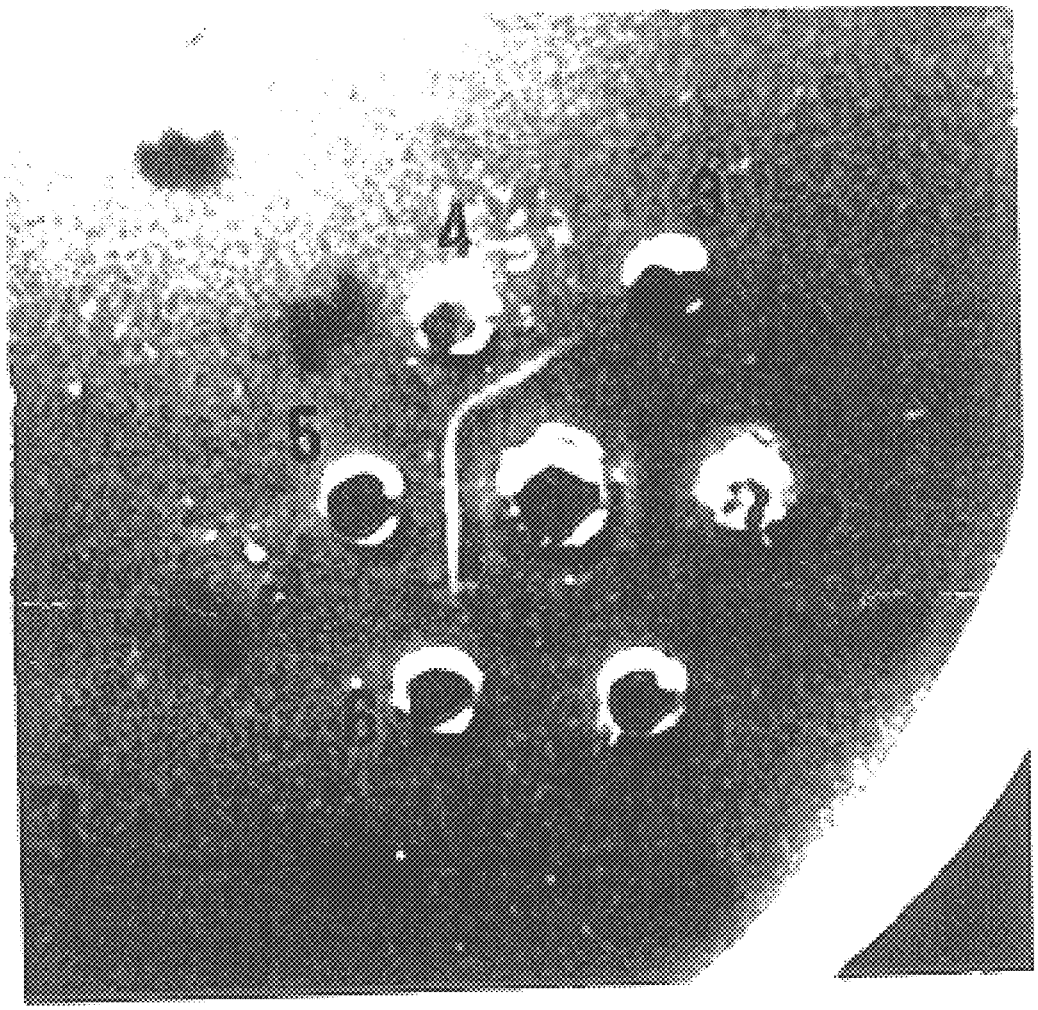
FIG. 3 shows a double agar Ouchterlony immunodiffusion assay for the presence of soy protein in kernels from corn strain 27-1. As in FIG. 2, the central well contains the antibody and peripheral wells 1–3 contain proteins from the mRNA-treated kernels which do not exhibit an additional band; wella 4 and 5 contain proteins from the mRNA-treated kernels demonstrating an additional band. A precipitation line is apparent in these samples. As in FIG. 2, well 6 is a negative control.
Figure 4:
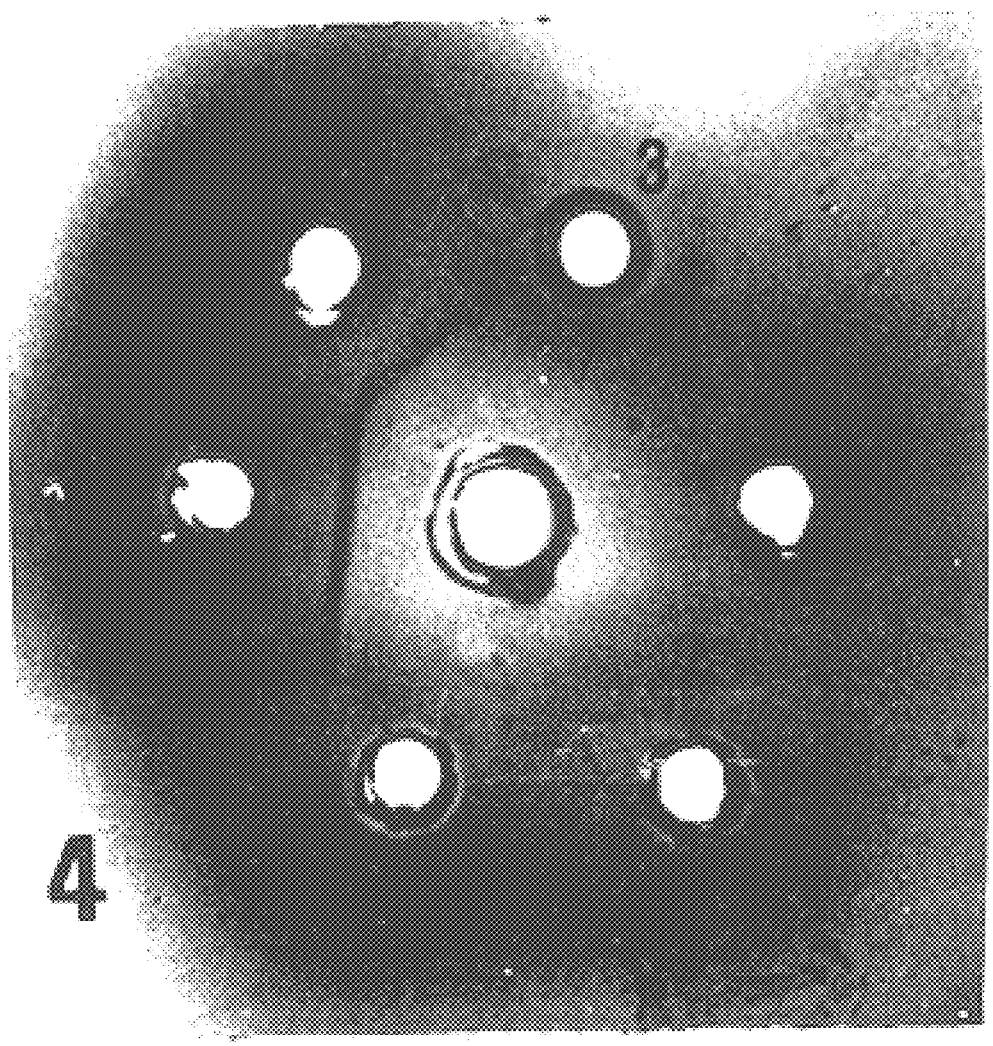
FIG. 4 shows results obtained when precipitation lines in FIG. 2 are stained with Coomassie brilliant blue. As can be seen in the Figure, the intensity of the precipitation lines varies from sample to sample.

The Ouchterlony Double Agar Diffusion Test: Based on the results from the SDS-PAGE, corn kernel-extracted protein with and without the additional band, and from the control kernels, were subjected to the double agar diffusion test with rabbit anti-soy protein serum. All of the corn protein with the additional band reacted to the anti-serum as shown by the precipitation line, but varied in intensity. See FIGS. 2–4 and Table 2, below:

TABLE 2

RESULTS OF THE DOUBLE AGAR DIFFUSION TEST.

| | EXPERIMENTS | | CONTROL |
|---|---|---|---|
| | mRNA TREATED SERIES | | |
| RESULTS | 29 SAMPLES WITH AN ADDITIONAL BAND | 105 SAMPLES WITHOUT AN ADDITIONAL BAND | 10 UNTREATED SAMPLES |
| IMMUNO-REACTION | 4+, 2+, + | NONE | NONE |

NOTE:
STRONG REACTION = 4+, POSITIVE REACTION = 2+, WEAK REACTION = +

No precipitation line was found in the control, nor in the corn proteins obtained from samples not expressing the additional band.

Figure 5:
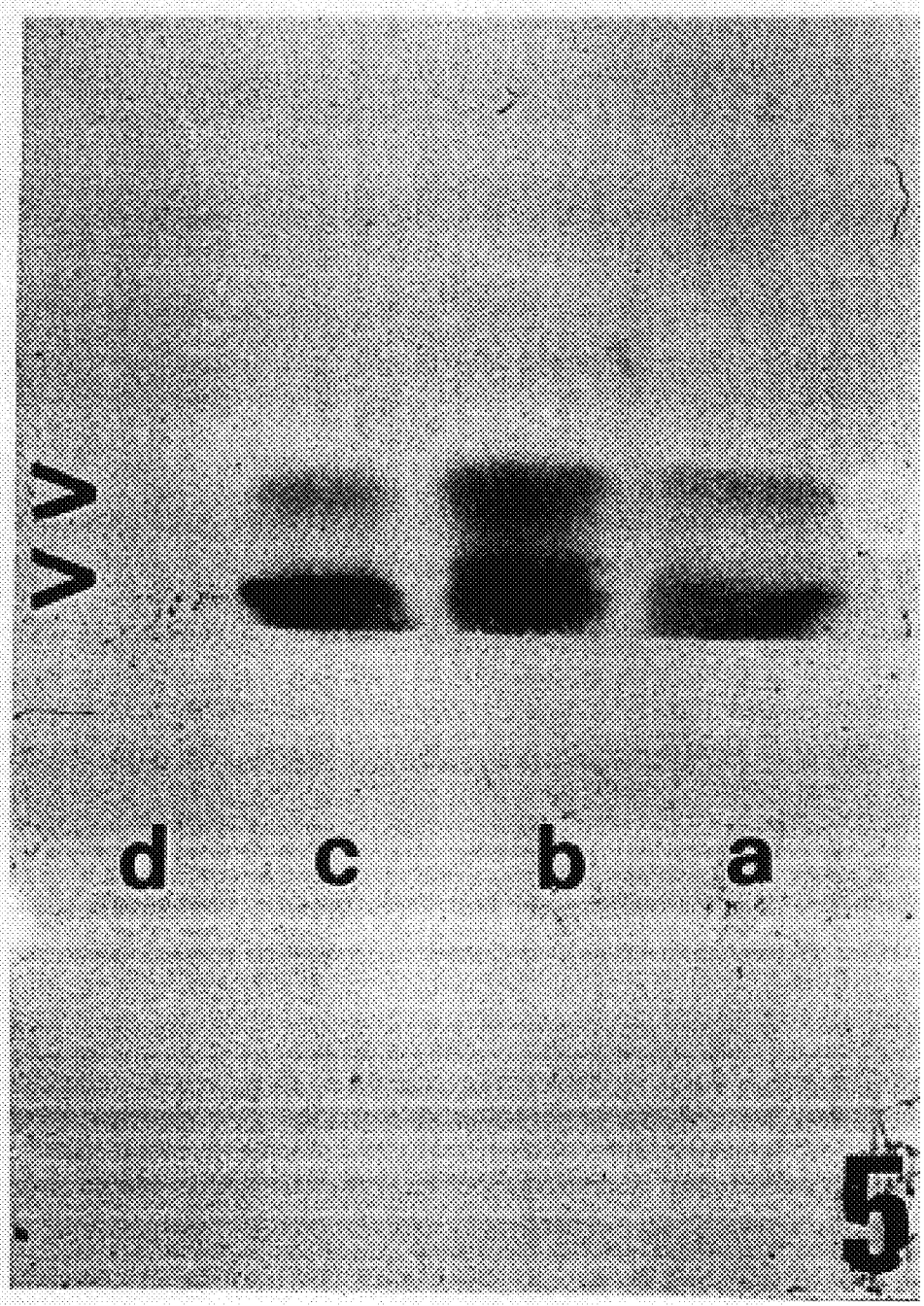
FIG. 5 illustrates detection of soy protein in transformed corn using SDS-PAGE gel electropheresis followed by Western blotting. Soy globulin is detected in lanes a, b, and c. Lane d contains the negative control extract.

Extracts from the kernels of the second generation of corn were analyzed as follows: The Western Blotting Technique: The kernels of the first generation were planted and harvested as the second generation. The kernel extracts from this second generation were subjected to the Western blotting technique. The results were that two bands appeared between 60–70 KD. See FIG. 5, lanes a, b, and c. No band was observed in the control, lane d. The demonstration of soy protein in the kernels of the second generation of corn illustrates that the soy mRNA transferred genetic information into the corn genome, such that soy globulin protein is expressed in the next generation.

Figure 6:
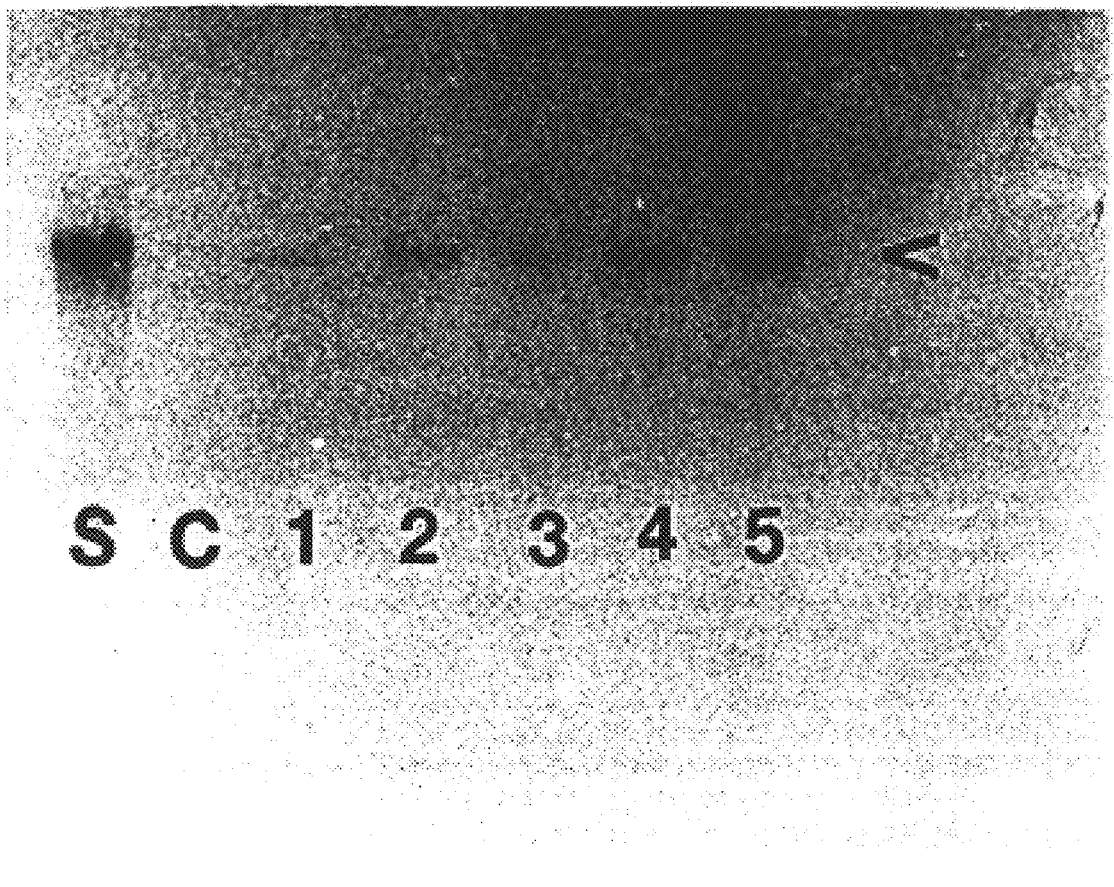
FIG. 6 is a representative autoradiogram of a Southern blot showing the hybridization of a $^{32}$P-labeled soy globulin DNA probes to genomic DNA isolated from corn.

Southern Blotting: Finding the soy protein in the second and succeeding generations of corn indicates that the mRNA encoded genetic information has been reverse transcribed and incorporated into the corn genome. This is presumably due to the presence of reverse transcriptase in the corn seed. Southern blotting demonstrated presence of soy globulin encoding DNA in the transformed corn. The results are shown in FIG. 6. The presence of the hybridizing band provides evidence of reverse transcription of the injected soy mRNA. See lanes 1–5. No soy derived nucleic acid sequences were detected in DNA obtained from untreated corn. See FIG. 6.

Identification of soy protein in the corn was carried out in three steps. The first method employed was SDS-PAGE. An additional band from the corn extract grown from the mRNA-treated kernels (shown by an arrow in FIG. 1) is observed. This band is absent in extracts isolated from untreated corn. Second, the extract of kernels exhibiting the additional band were analyzed by an Ouchterlony double agar immunodiffusion test using rabbit anti-soy protein serum. A precipitation line was found between the anti-serum and the extract from the kernels exhibiting an additional band by SDS-PAGE (Table 2, FIGS. 2–4). No line appeared between the anti-serum and the control extract. Third, in order to see if the soy protein globulin was expressed in the next generation of corn, the kernels of the first generation were planted again. The corn grown from these kernels was harvested and the protein extracts analyzed by Western blotting. The results of this experiment showed the appearance of two bands (FIG. 5) believed to represent the two globulins of the soy protein, 7S and 11S (1).

Finally, the presence of soy globulin encoding nucleic acids in mRNA treated corn was demonstrated by Southern hybridization assays using $^{32}$P-labeled soy specific probes.

While the preferred embodiments of this invention have been described and specifically exemplified above, the invention is not limited to such embodiments. Modifications may be made thereto without departing from the scope and spirit of the present invention, as set forth in the following claims and equivalents thereto not reading on the prior art.

What is claimed is:

1. A transgenic corn plant expressing soy globulin protein.
2. Transgenic corn kernels expressing soy globulin protein.

* * * * *